US006852814B2

(12) United States Patent
Dershem et al.

(10) Patent No.: US 6,852,814 B2
(45) Date of Patent: Feb. 8, 2005

(54) THERMOSETTING RESIN COMPOSITIONS CONTAINING MALEIMIDE AND/OR VINYL COMPOUNDS

(75) Inventors: Stephen M. Dershem, San Diego, CA (US); Dennis B. Patterson, Palmdale, CA (US); Jose A. Osuna, Jr., Albany, OR (US)

(73) Assignee: Henkel Corporation, CT (US)

( * ) Notice: Subject to any disclaimer, the term of this patent is extended or adjusted under 35 U.S.C. 154(b) by 55 days.

(21) Appl. No.: 10/084,389

(22) Filed: Feb. 25, 2002

(65) Prior Publication Data

US 2002/0193541 A1 Dec. 19, 2002

(Under 37 CFR 1.47)

Related U.S. Application Data

(63) Continuation of application No. 09/580,026, filed on May 26, 2000, which is a continuation-in-part of application No. 09/107,897, filed on Jun. 29, 1998, now Pat. No. 6,187,886, which is a continuation-in-part of application No. 08/711,982, filed on Sep. 10, 1996, now Pat. No. 5,789,757, which is a continuation-in-part of application No. 08/300,721, filed on Sep. 2, 1994, now Pat. No. 6,034,194.

(51) Int. Cl.$^7$ ............................................. C08F 222/40
(52) U.S. Cl. ...................... 526/262; 524/439; 524/506; 524/516; 524/850; 525/282; 525/205; 525/322; 522/60; 522/61; 522/176; 522/173; 522/164
(58) Field of Search .......................... 526/262; 524/439, 524/506, 516, 850; 525/282, 205, 322; 522/164, 173, 176, 60, 61

(56) References Cited

U.S. PATENT DOCUMENTS

| | | | |
|---|---|---|---|
| 4,323,662 A | * 4/1982 | Oba et al. ................... 525/281 |
| 4,369,302 A | * 1/1983 | Ikeguchi et al. .............. 528/73 |
| 4,564,663 A | * 1/1986 | Martin et al. ................ 526/262 |
| 4,740,343 A | * 4/1988 | Gaku et al. .................. 264/225 |
| 4,740,830 A | * 4/1988 | Ketley ........................ 257/741 |
| 4,766,179 A | * 8/1988 | De Koning ................. 525/282 |
| 4,853,449 A | * 8/1989 | Domeier ..................... 526/259 |
| 4,876,358 A | * 10/1989 | Alexander ................... 548/521 |
| 4,886,842 A | * 12/1989 | Drain et al. ................. 522/103 |
| 5,358,992 A | * 10/1994 | Dershem et al. ............. 524/439 |
| 5,359,020 A | 10/1994 | Bunner et al. ............... 526/262 |
| 5,364,700 A | 11/1994 | Domeier ..................... 428/394 |
| 5,380,768 A | 1/1995 | Cranston et al. ............. 521/167 |
| 5,405,686 A | 4/1995 | Portelli et al. ............... 428/229 |
| 5,442,039 A | 8/1995 | Hefner, Jr. et al. .......... 528/422 |
| 5,447,988 A | * 9/1995 | Dershem et al. ............. 524/780 |
| 5,470,920 A | 11/1995 | Camberlin et al. .......... 525/421 |
| 5,475,048 A | 12/1995 | Jamison et al. ............. 524/439 |
| 5,483,101 A | 1/1996 | Shimoto et al. ............ 257/701 |
| 5,489,641 A | * 2/1996 | Dershem ..................... 524/439 |
| 5,527,592 A | 6/1996 | Afzali-Ardakani et al. . 428/209 |
| 5,536,970 A | * 7/1996 | Higashi et al. .............. 257/676 |
| 5,599,611 A | 2/1997 | Afzali-Ardakani et al. . 442/180 |

FOREIGN PATENT DOCUMENTS

EP        0 318 162 A2   10/1988   ....... C07D/207/452

OTHER PUBLICATIONS

Romenesko, B., *Ball Grid Array & Flip Chip Technologies: Their Histories & Prospects*, vol. 19, No. 1, The International Journal of Microcircuits & Electronic Packaging, (1996).

Smith, Mark A., et al, Bismaleimide/Vinyl Ether Matrix Copolymers, pp. 337–338.

Roderick, William, "Deydration of N–(p–Chloropheynl) phthalamic Acid by Acetic and Trifluoroacetic Anhydrides", vol. 29, pp. 745–747 (1964).

Cotter, Robert, J., et al, "The Synthesis of N–Substituted Isomaleimides", pp. 10–15, (1960).

* cited by examiner

*Primary Examiner*—James J. Seidleck
*Assistant Examiner*—Sanza L. McClendon
(74) *Attorney, Agent, or Firm*—Fitzpatrick, Cella, Harper & Scinto

(57) ABSTRACT

In accordance with the present invention, there are provided novel thermosetting resin compositions which do not require solvent to provide a system having suitable viscosity for convenient handling. Invention compositions have the benefit of undergoing rapid cure. The resulting thermosets are stable to elevated temperatures, are highly flexible, have low moisture uptake and are consequently useful in a variety of applictions, e.g., in adhesive applications since they display good adhesion to both the substrate and the device attached thereto.

11 Claims, No Drawings

THERMOSETTING RESIN COMPOSITIONS CONTAINING MALEIMIDE AND/OR VINYL COMPOUNDS

RELATED APPLICATIONS

This application is a continuation of U.S. patent application Ser. No. 09/580,026, filed May 26, 2000, which is a continuation-in-part of U.S. patent application Ser. No. 09/107,897, filed Jun. 29, 1998, now U.S. Pat. No. 6,187,886, which itself is a continuation-in-part of U.S. patent application Ser. No. 08/711,982, filed Sep. 10, 1996 (now U.S. Pat. No. 5,789,757); this application also claims the benefit of an earlier effective filing date from U.S. patent application Ser. No. 08/460,495, filed Jun. 2, 1995 (now U.S. Pat. No. 6,034,195), which is a continuation-in-part of U.S. patent application Ser. No. 08/300,721, filed Sep. 2, 1994 (now U.S. Pat. No. 6,034,194), the disclosures of each of which are hereby expressly incorporated herein by reference.

FIELD OF THE INVENTION

The present invention relates to thermosetting resin compositions and uses therefor. In a particular aspect, the present invention relates to thermosetting resin compositions containing maleimide resins, vinyl resins, or both.

BACKGROUND OF THE INVENTION

Bismaleimides per se occupy a prominent position in the spectrum of thermosetting resins. Indeed, several bismaleimides are commercially available. Bismaleimide resins are used as starting materials for the preparation of thermoset polymers possessing a wide range of highly desirable physical properties. Depending on the particular resin and formulation, the resins provide cured products having excellent storage stability, heat resistance, as well as good adhesive, electrical and mechanical properties. Accordingly, bismaleimide resins have been used for the production of moldings, heat-resistant composite materials, high temperature coatings and for the production of adhesive joints. Typically, however, in any particular resin formulation there is a trade-off between the various properties. For example, in the formulation of "snap" cure adhesives (i.e., adhesives that cure in two minutes or less at $\leq 200°$ C.), it is desirable to use a system which does not require the addition of diluent to facilitate handing. In other words, snap cure products require formulations containing 100% reactive materials. Thus, it is desirable to prepare snap cure resins which are liquid at or about room temperature (i.e., low viscosity materials) for ease of handling.

Unfortunately, up until now, it has not proved possible to formulate bismaleimide compositions that are both quick curing, easy to handle (i.e., liquid at or about room temperature), and have low moisture uptake. Consequently, it is a desideratum to provide thermosetting bismaleimide resin compositions that produce cured resins exhibiting a combination of highly desirable physical properties, including a combination of rapid curing and low water absorption.

A particular disadvantage of the use of bismaleimide resins for the types of applications described above is that, at room temperature, such materials exist as solid resins which require the addition of liquid diluents, in order for such resins to achieve a useful and processable viscosity. This difficulty has been compounded by the poor solubility of bismaleimides in organic solvents. This poor solubility generally necessitates the use of polar diluents, such as N-methyl-2-pyrrolidone or dimethylformamide. These diluents are undesirable, inter alia, from the viewpoint of environmental pollution. Therefore, it is another desideratum to provide bismaleimide resins that require little, if any, non-reactive diluent to facilitate handling.

One approach to solving the problem of a need for a diluent has been to use reactive liquid diluents. For example, the co-cure of simple bismaleimides with relatively simple divinyl ethers is known in the art. The use of such diluents is advantageous in that these materials become incorporated into the thermosetting resin composition, and hence do not create disposal problems. However, the range of suitable liquid reactive diluents is very limited. Many of the available diluents are restricted by the low boiling points thereof, and, therefore, the high volatility thereof; by the odor of such materials; by the toxicity of such materials and/or problems with skin irritation induced thereby; by the poor ability of such materials to solubilize bismaleimides; by the high viscosity of such materials, which, again, limits the bismaleimide solubility and also leads to little or no tack in the formulation; by the poor thermal stability and/or hydrolytic stability of such materials; by the incompatibility of such materials with other formulation modifiers, and the like. In particular, since the diluents become an integral component of the thermosetting resin composition, they necessarily influence its properties. Consequently, it is another desideratum to provide combinations of bismaleimide resins with reactive diluents which do not suffer from the above-described drawbacks and that produce cured resins exhibiting a combination of highly desirable physical properties, including rapid curing and low water absorption.

Accordingly, there has existed a definite need for bismaleimide resins that produce cured resins exhibiting a combination of highly desirable physical properties, including rapid curing and low water absorption. There has existed a further need for bismaleimide resins that require the additions of little, if any, non-reactive diluent to facilitate handling. And there has existed a still further need for combinations of bismaleimide resins with reactive diluents which do not suffer from the limitations of known reactive resins and that produce cured resins exhibiting a combination of highly desirable physical properties, including rapid curing and low water absorption. The present invention satisfies these and other needs and provides further related advantages.

BRIEF DESCRIPTION OF THE INVENTION

In accordance with the present invention, we have developed novel thermosetting resin compositions which meet all of the above-described needs, i.e., produce cured resins exhibiting a combination of highly desirable physical properties, including rapid curing and low water absorption, and which require little, if any, diluent to provide a system of suitable viscosity for convenient handling. In another aspect of the invention, we have developed novel combinations of bismaleimide resins with reactive diluents, which do not suffer from the limitations of known reactive resins and that produce cured resins exhibiting a combination of highly desirable physical properties, including rapid curing and low water absorption. The resulting cured resins are stable at elevated temperatures, are highly flexible, have low moisture uptake and good adhesion.

DETAILED DESCRIPTION OF THE INVENTION

In accordance with the present invention, there are provided novel maleimide resins of general formula I, as follows:

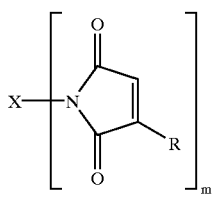

wherein:
m=1, 2 or 3,
each R is independently selected from hydrogen or lower alkyl, and
X is a monovalent or polyvalent radical selected from:
high molecular weight branched chain alkyl, alkylene or alkylene oxide species having from about 12 to about 500 atoms in the backbone thereof,
aromatic groups having the structure:

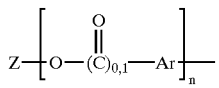

wherein:
n=1, 2 or 3,
each Ar is a monosubstituted, disubstituted or trisubstituted aromatic or heteroaromatic ring having in the range of 3 up to 10 carbon atoms, and
Z is a high molecular weight branched chain alkyl, alkylene or alkylene oxide species having from about 12 to about 500 atoms in the backbone thereof,
as well as mixtures thereof.

It is a distinct advantage of the bismaleimide resins of Formula I that they can be used with little, if any, added diluent. Generally, for easy handling and processing, the viscosity of a thermosetting resin composition must fall in the range of about 10 to about 12,000 centipoise, preferably from about 10 to about 2,000 centipoise. Maleimide resins of Formula I typically require no added diluent, or when diluent is used with resins contemplated by Formula I, far less diluent is required to facilitate handling than must be added to conventional maleimide-containing thermosetting resin systems. Preferred maleimide resins of Formula I include stearyl maleimide, oleyl maleimide and behenyl maleimide, 1,20-bismaleimido-10,11-dioctyl-eicosane (which likely exists in admixture with other isomeric species produced in the ene reactions employed to produce dimer acids from which the bismaleimide is prepared, as discussed in greater detail below), and the like, as well as mixtures of any two or more thereof.

When a diluent is added, it can be any diluent which is inert to the bismaleimide resin and in which the resin has sufficient solubility to facilitate handling. Representative inert diluents include dimethylformamide, dimethylacetamide, N-methylpyrrolidone, toluene, xylene, methylene chloride, tetrahydrofuran, methyl ethyl ketone, monoalkyl or dialkyl ethers of ethylene glycol, polyethylene glycol, propylene glycol or polypropylene glycol, glycol ethers, and the like.

Alternatively, the diluent can be any reactive diluent which, in combination with bismaleimide resin, forms a thermosetting resin composition. Such reactive diluents include acrylates and methacrylates of monofunctional and polyfunctional alcohols, vinyl compounds as described in greater detail herein, styrenic monomers (i.e., ethers derived from the reaction of vinyl benzyl chlorides with mono-, di-, or trifunctional hydroxy compounds), and the like.

Now in accordance with the invention there has been found an especially preferred class of reactive diluents corresponding to vinyl or polyvinyl compounds having the general formula:

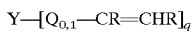

wherein:
q is 1, 2 or 3,
each R is independently as defined above,
each Q is independently selected from —O—, —O—C(O)—, —C(O)— or —C(O)—O—, and
Y is selected from:
saturated straight chain alkyl, alkylene or alkylene oxide, or branched chain alkyl, alkylene or alkylene oxide, optionally containing saturated cyclic moieties as substituents on said alkyl, alkylene or alkylene oxide chain or as part of the backbone of the alkyl, alkylene or alkylene oxide chain, wherein said alkyl, alkylene or alkylene oxide species have at least 6 carbon atoms, preferably wherein said alkyl, alkylene or alkylene oxide species are high molecular weight branched chain species having from about 12 to about 500 carbon atoms,
aromatic moieties having the structure:

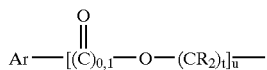

wherein each R is independently as defined above, Ar is as defined above, t falls in the range of 2 up to 10 and u is 1, 2 or 3,
polysiloxanes having the structure:

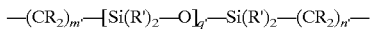

wherein each R is independently defined as above, and each R' is independently selected from hydrogen, lower alkyl or aryl, m' falls in the range of 1 up to 10, n' falls in the range of 1 up to 10, and q' falls in the range of 1 up to 50,
polyalkylene oxides having the structure:

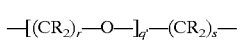

wherein each R is independently as defined above, r falls in the range of 1 up to 10, s falls in the range of 1 up to 10, and q' is as defined above,
as well as mixtures of any two or more thereof.

Exemplary vinyl or polyvinyl compounds embraced by the above generic structure include stearyl vinyl ether, behenyl vinyl ether, eicosyl vinyl ether, isoeicosyl vinyl ether, isotetracosyl vinyl ether, poly(tetrahydrofuran) divinyl ether, tetraethylene glycol divinyl ether, tris-2,4,6-(1-vinyloxybutane-4-)oxy-1,3,5-triazine, bis-1,3-(1-vinyloxybutane-4-)oxycarbonyl-benzene (alternately referred to as bis(4-vinyloxybutyl)isophthalate; available from Allied-Signal Inc., Morristown, N.J., under the trade name Vectomer™ 4010), divinyl ethers prepared by transvinylation between lower vinyl ethers and higher molecular weight di-alcohols (e.g., α, ω-dihydroxy hydrocarbons prepared from dimer acids, as described above; an exemplary divinyl ether which can be prepared from such dimer alcohols is 10,11-dioctyl eicosane-1,20-divinyl ether, which would likely exist in admixture with other isomeric species produced in ene reactions employed to produce dimer acids), in the presence of a suitable palladium catalyst (see, for example, Example 9), optionally hydrogenated α,ω-disubstituted polybutadienes, optionally hydrogenated α,ω-disubstituted polyisoprenes, optionally hydrogenated α,ω-disubstituted poly[(1-ethyl)-1,2-ethane], and the like. Preferred divinyl resins include stearyl vinyl ether, behenyl vinyl ether, eicosyl vinyl ether, isoeicosyl vinyl ether, poly(tetrahydrofuran) divinyl ether, divinyl ethers prepared by transvinylation between lower vinyl ethers and higher molecular weight di-alcohols (e.g., α,ω-dihydroxy hydrocarbons prepared from dimer acids, as described above; an exemplary divinyl ether which can be prepared from such dimer alcohols is 10,11-dioctyl eicosane-1,20-divinyl ether, which would likely exist in admixture with other isomeric species produced in ene reactions employed to produce dimer acids), in the presence of a suitable palladium catalyst (see, for example, Example 9), and the like.

Additionally, in accordance with another embodiment of the present invention, it has been found that divinyl compounds corresponding to Formula II where —Q— is —C(O)—O— and Y is a high molecular weight branched chain alkylene species having from about 12 to about 500 carbon atoms are useful thermosetting resin compositions, even in the absence of bismaleimide resins. When combined with suitable amounts of at least one free radical initiator and at least one coupling agent, these divinyl ether resins, alone, are capable of forming thermosetting resin compositions exhibiting excellent physical properties, including rapid cure rates and low water absorption.

In accordance with yet another embodiment of the present invention, there are provided thermosetting resin compositions made of mixtures of a vinyl compound of Formula II and a maleimide corresponding to the following general formula (generally containing in the range of about 0.01 up to about 10 equivalents of vinyl compound per equivalent of maleimide with in the range of about 0.01 up to about 1 eq. being preferred where the vinyl compound is a mono- or polyvinyl ether):

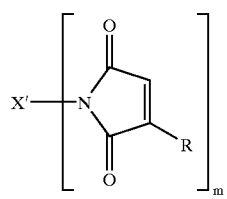

(III)

wherein:
m is as defined above,
each R is independently as defined above, and
X' is a monovalent or polyvalent radical selected from:
saturated straight chain alkyl or alkylene, or branched chain alkyl or alkylene, optionally containing saturated cyclic moieties as substituents on said alkyl or alkylene chain or as part of the backbone of the alkyl or alkylene chain, wherein said alkyl or alkylene species have at least 6 carbon atoms, preferably wherein said alkyl or alkylene species are high molecular weight branched chain species having from about 12 to about 500 carbon atoms, aromatic groups having the structure:

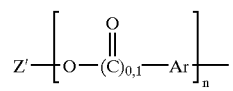

wherein
n is as defined above, Ar is as defined above, and Z' is a monovalent or polyvalent radical selected from:
saturated straight chain alkyl or alkylene, or branched chain alkyl or alkylene, optionally containing saturated cyclic moieties as substituents on said alkyl or alkylene chain or as part of the backbone of the alkyl or alkylene chain, wherein said species have at least 6 carbon atoms, preferably wherein said species are high molecular weight branched chain species having from about 12 to about 500 atoms as part of the backbone thereof, siloxanes having the structure:

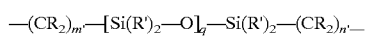

wherein each R and R' is independently defined as above, and wherein each of m', n' and q is as defined above, polyalkylene oxides having the structure:

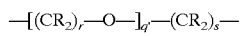

wherein each R is independently as defined above, and wherein each of r, s and q' is as defined above, aromatic moieties having the structure:

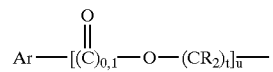

wherein each R is independently as defined above, Ar is as defined above, and each of t and u is as defined above, siloxanes having the structure:

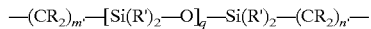

wherein each R and R' is independently defined as above, and wherein each of m', n' and q' is as defined above, polyalkylene oxides having the structure:

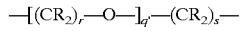

wherein each R is independently as defined above, and wherein each of r, s and q' is as defined above,
as well as mixtures of any two or more thereof.

Such mixtures possess a combination of highly desirable physical properties, including both rapid cure rates and low water absorption.

Exemplary bismaleimides embraced by Formula III include bismaleimides prepared by reaction of maleic anhydride with dimer amides (i.e., α, ω-diamino hydrocarbons prepared from dimer acids, a mixture of mono-, di- and tri-functional oligomeric, aliphatic carboxylic acids; dimer acids are typically prepared by thermal reaction of unsaturated fatty acids, such as oleic acid, linoleic acid, and the like, which induces an ene reaction, leading to the above-mentioned mixture of components). An exemplary bismaleimide which can be prepared from such dimer amides is 1,20-bismaleimido-10,11-dioctyl-eicosane, which would likely exist in admixture with other isomeric species produced in the ene reactions employed to produce dimer acids. Other bismaleimides contemplated for use in the practice of the present invention include bismaleimides prepared from α,ω-aminopropyl-terminated polydimethyl siloxanes (such as "PS510" sold by Hüls America, Piscataway, N.J.), polyoxypropylene amines (such as "D-230", "D-400", "D-2000" and "T-403", sold by Texaco Chemical Company, Houston, Tex.), polytetramethyleneoxide-di-p-aminobenzoates (such as the family of such products sold by Air Products, Allentown, Pa., under the trade name "Versalink" e.g., "Versalink P-650"), and the like. Preferred maleimide resins of Formula III include stearyl maleimide, oleyl maleimide, behenyl maleimide, 1,20-bismaleimido-10,11-dioctyl-eicosane (which likely exists in admixture with other isomeric species produced in the ene reactions employed to produce dimer acids from which the bismaleimide is prepared, as discussed in greater detail elsewhere in this specification), and the like, as well as mixtures of any two or more thereof.

In preferred embodiments of the present invention, when mixtures of bismaleimides and divinyl compounds are employed, either X' (of the bismaleimide) or Y (of the divinyl compound) can be aromatic, but both X' and Y are not both aromatic in the same formulation. Additionally, in preferred embodiments of the present invention, when mixtures of bismaleimides and divinyl compounds are employed, at least one of X' or Y is a high molecular weight branched chain alkylene species having from about 12 to about 500 carbon atoms.

Bismaleimides can be prepared employing techniques well known to those of skill in the art. The most straightforward preparation of maleimide entails formation of the maleamic acid via reaction of the corresponding primary amine with maleic anhydride, followed by dehydrative closure of the maleamic acid with acetic anhydride. A major complication is that some or all of the closure is not to the maleimide, but to the isomaleimide. Essentially the isomaleimide is the dominant or even exclusive kinetic product, whereas the desired maleimide is the thermodynamic product. Conversion of the isomaleimide to the maleimide is effectively the slow step and, particularly in the case of aliphatic amides, may require forcing conditions which can lower the yield. Nevertheless, in the case of a stable backbone such as that provided by a long, branched chain hydrocarbon (e.g., $-(CH_2)_9-CH(C_8H_{17})-CH(C_8H_{17})-(CH_2)_9-$), the simple acetic anhydride approach appears to be the most cost effective method. Of course, a variety of other approaches can also be employed.

For example, dicyclohexylcarbodiimide (DCC) closes maleamic acids much more readily than does acetic anhydride. With DCC, the product is exclusively isomaleimide. However, in the presence of suitable isomerizing agents, such as 1-hydroxybenzotriazole (HOBt), the product is solely the maleimide. The function of the HOBt could be to allow the closure to proceed via the HOBt ester of the maleamic acid (formed via the agency of DCC) which presumably closes preferentially to the maleimide. However, it is unclear why such an ester should exhibit such a preference. In any case, it is demonstrated herein that isomide generated by reaction of the bismaleamic acid of 10,11-dioctyleicosane with either acetic acid anhydride or EEDQ (2-ethoxy-1-ethoxycarbonyl-1,2-dihydroquinoline) is isomerized to the bismaleimide by catalytic amounts of HOBt. 3-Hydroxy-1,2,3-benzotriazine-4-one appears to be at least as effective as HOBt in effecting this isomerization, whereas N-hydroxysuccinimide is substantially less so.

Likely, isomerizing agents such as HOBt add to the isoimide to yield the amic acid ester. If this exhibits any tendency whatsoever to close to the imide, much less a strong bias for doing so, a route for interconverting isoimide and imide is thereby established and the thermodynamic product, imide, should ultimately prevail. Thus if the initial closure of ester formed in the DCC reaction yields any isoimide, or if any isoimide is produced by direct closure of the acid, the situation will be subsequently "corrected" via conversion of the isoimide to the imide by the action of the active ester alcohol as an isomerizing agent.

One problem encountered with bismaleimides is a proclivity for oligomerization. This oligomerization is the principle impediment to yield in the synthesis of bismaleimides, and may present problems in use. Radical inhibitors can mitigate this potential problem somewhat during the synthesis but these may be problematic in use. Fortunately, oligomer may be removed by extracting the product into pentane, hexane or petroleum ether, in which the oligomers are essentially insoluble.

Thermosetting resin compositions of the invention also contain in the range of 0.2 up to 3 wt % of at least one free radical initiator, based on the total weight of organic materials in the composition, i.e., in the absence of filler. As employed herein, the term "free radical initiator" refers to any chemical species which, upon exposure to sufficient energy (e.g., light, heat, or the like), decomposes into two parts which are uncharged, but which each possesses at least one unpaired electron. Preferred as free radical initiators for use in the practice of the present invention are compounds which decompose (i.e., have a half life in the range of about 10 hours) at temperatures in the range of about 70 up to 180° C.

Exemplary free radical initiators contemplated for use in the practice of the present invention include peroxides (e.g., dicumyl peroxide, dibenzoyl peroxide, 2-butanone peroxide, tert-butyl perbenzoate, di-tert-butyl peroxide, 2,5-bis(tert-butylperoxy)-2,5-dimethylhexane, bis(tert-butyl peroxyisopropyl)benzene, and tert-butyl hydroperoxide), azo compounds (e.g., 2,2'-azobis(2-methylpropanenitrile), 2,2'-azobis(2-methylbutanenitrile), and 1,1'-azobis (cyclohexanecarbonitrile)), and the like. Peroxide initiators are presently preferred because they entail no gas release upon decomposition into free radicals. Those of skill in the art recognize, however, that in certain adhesive applications, the release of gas (e.g. $N_2$) during cure of the adhesive would be of no real concern. Generally in the range of about 0.2 up to 3 wt % of at least one free radical initiator (based on the total weight of the organic phase) will be employed, with in the range of about 0.5 up to 1.5 wt % preferred.

Thermosetting resin compositions of the invention possess a variety of physical properties making them particularly adapted for use in the preparation of "snap" cure adhesives. Such adhesives are useful, for example, in die attach applications. When used in adhesive applications, it is desirable to add coupling agent(s) to the formulation.

As employed herein, the term "coupling agent" refers to chemical species that are capable of bonding to a mineral surface and which also contain polymerizably reactive functional group(s) so as to enable interaction with the adhesive composition. Coupling agents thus facilitate linkage of the adhesive composition to the substrate to which it is applied.

Exemplary coupling agents contemplated for use in the practice of the present invention include silicate esters, metal acrylate salts (e.g., aluminum methacrylate), titanates (e.g., titanium methacryloxyethylacetoacetate triisopropoxide), or compounds that contain a copolymerizable group and a chelating ligand (e.g., phosphine, mercaptan, acetoacetate, and the like). Generally in the range of about 0.1 up to 10 wt % of at least one coupling agent (based on the total weight of the organic phase) will be employed, with in the range of about 0.5 up to 2 wt % preferred.

Presently preferred coupling agents contain both a co-polymerizable function (e.g., vinyl moiety, acrylate moiety, methacrylate moiety, styrene moiety, cyclopentadiene moiety, and the like), as well as a silicate ester function. The silicate ester portion of the coupling agent is capable of condensing with metal hydroxides present on the mineral surface of the substrate, while the co-polymerizable function is capable of co-polymerizing with the other reactive components of invention adhesive composition. Especially preferred coupling agents contemplated for use in the practice of the invention are oligomeric silicate coupling agents such as poly(methoxyvinylsiloxane).

In addition to the incorporation of coupling agents into invention adhesive compositions, it has also been found that the optional incorporation of a few per cent of the precursor bismaleamic acid greatly increases adhesion. Indeed, good adhesion is retained even after strenuous exposure to water.

Adhesive compositions of the invention possess a combination of physical properties believed to be critical to successful commercial application:

1. The adhesive compositions have good handling properties, needing little, if any, inert diluent added thereto (i.e., the resin compositions form 100% reactive systems of sufficiently low viscosity);
2. The adhesive compositions are capable of rapid ("snap") cure, i.e., curing in two minutes or less (preferably as short as 15 seconds) at $\leq 200°$ C.;
3. The resulting thermosets are stable to at least 250° C., wherein "stable" is defined as less than 1% weight loss at 250° C. when subjected to a temperature ramp of 10° C./min. in air via thermogravimetric analysis (TGA);
4. The resulting thermosets are sufficiently flexible (e.g., radius of curvature >1.0 meter for a 300 mil$^2$ silicone die on a copper lead frame using a cured bond line $\leq 2$ mils) to allow use in a variety of high stress applications;
5. The resulting thermosets exhibit low-moisture uptake (in nonhermetic packages); and
6. The resulting thermosets exhibit good adhesion to substrates, even after strenuous exposure to moisture.

Adhesive compositions of the invention can be employed in the preparation of die-attach pastes comprising in the range of about 10 up to 80 wt % of the above-described thermosetting resin composition, and in the range of about 20 up to 90 wt % filler. Fillers contemplated for use in the practice of the present invention can be electrically conductive and/or thermally conductive, and/or fillers which act primarily to modify the rheology of the resulting composition. Examples of suitable electrically conductive fillers which can be employed in the practice of the present invention include silver, nickel, copper, aluminum, palladium, gold, graphite, metal-coated graphite (e.g., nickel-coated graphite, silver-coated graphite, and the like), and the like. Examples of suitable thermally conductive fillers which can be employed in the practice of the present invention include graphite, aluminum nitride, silicon carbide, boron nitride, diamond dust, alumina, and the like. Compounds which act primarily to modify rheology include fumed silica, alumina, titania, high surface area smectite clays, and the like.

In accordance with yet another embodiment of the present invention, there are provided assemblies of components adhered together employing the above-described adhesive compositions and/or die attach compositions. Thus, for example, assemblies comprising a first article permanently adhered to a second article by a cured aliquot of the above-described adhesive composition are provided. Articles contemplated for assembly employing invention compositions include memory devices, ASIC devices, microprocessors, flash memory devices, and the like.

Also contemplated are assemblies comprising a microelectronic device permanently adhered to a substrate by a cured aliquot of the above-described die attach paste. Microelectronic devices contemplated for use with invention die attach pastes include copper lead frames, Alloy 42 lead frames, silicon dice, gallium arsenide dice, germanium dice, and the like.

In accordance with still another embodiment of the present invention, there are provided methods for adhesively attaching two component parts to produce the above-described assemblies. Thus, for example, a first article can be adhesively attached to a second article, employing a method comprising:

(a) applying the above-described adhesive composition to said first article,
(b) bringing said first and second article into intimate contact to form an assembly wherein said first article and said second article are separated only by the adhesive composition applied in step (a), and thereafter,
(c) subjecting said assembly to conditions suitable to cure said adhesive composition.

Similarly, a microelectronic device can be adhesively attached to a substrate, employing a method comprising:

(a) applying the above-described die attach paste to said substrate and/or said microelectronic device,
(b) bringing said substrate and said device into intimate contact to form an assembly wherein said substrate and said device are separated only by the die attach composition applied in step (a), and thereafter,
(c) subjecting said assembly to conditions suitable to cure said die attach composition.

Conditions suitable to cure invention die attach compositions comprise subjecting the above-described assembly to a temperature of less than about 200° C. for about 0.25 up to 2 minutes. This rapid, short duration heating can be accomplished in a variety of ways, e.g., with an in-line heated rail, a belt furnace, or the like.

In accordance with a still further embodiment of the present invention, there is provided a method for the preparation of bismaleimides from diamines. The invention synthetic method comprises:

adding diamine to a solution of maleic anhydride,
adding acetic anhydride to said solution once diamine addition is complete, and then allowing the resulting mixture to stir overnight, and thereafter
treating the resulting reaction mixture with a suitable isomerizing agent.

Diamines contemplated for use in the practice of the present invention include saturated and unsaturated dimer diamines (such as the dimer amines sold by Henkel Corporation, Ambler, Pa., under the trade name "Versamine 552" and "Versamine 551"), α,ω-aminopropyl-terminated polydimethyl siloxanes (such as "PS510" sold by Hüls America, Piscataway, N.J.), polyoxypropylene amines (such as "D-230", "D-400", "D-2000" and "T-403", sold by Texaco Chemical Company, Houston, Tex.), polytetramethyleneoxide-di-p-aminobenzoate (such as the family of such products sold by Air Products, Allentown, Pa., under the trade name "Versalink" e.g., "Versalink P-650"), and the like. Diamine and maleic anhydride are typically combined in approximately equimolar amounts, with a slight excess of maleic anhydride preferred. Isomerizing agents contemplated for use in the practice of the present invention include 1-hydroxybenzotriazole, 3-hydroxy-1,2,3-benzotriazine-4-one, 1-hydroxy-7-azabenzotriazole, N-hydroxysuccinimide, and the like.

The invention will now be described in greater detail by reference to the following non-limiting examples.

EXAMPLE 1

Preparation of the bismaleimide of hydrogenated dimer acid diamine (Henkel Corp. Versamine 552) by closure of the bismaleamic acid with acetic anhydride to a mixture of isomaleimide and maleimide, followed by isomerization of the isomaleimide to maleimide with 1-hydroxybenzotriazole (HOBt) under mild conditions. A solution of 30.0 g of Versamine 552 in 90 mL of anhydrous tetrahydrofuran (THF) was slowly added to a solution of 12.5 g of maleic anhydride in 60 mL of THF. One hour after completion of the addition, 125 mL of acetic anhydride was added and the reaction mixture stirred overnight under argon atmosphere.

A Fourier transform infrared attenuated total reflectance (FTIR ATR) spectrum indicated substantial conversion of the amic acid to the isoimide, with little if any amide. The reaction mixture was brought to reflux and maintained there for three hours. FTIR now indicated a mixture of isoimide and maleimide with the former apparently (uncalibrated spectrum) predominating. Benzoquinone, 0.1 g, was added to the reaction mixture and the solvent/acetic anhydride/acetic acid stripped under vacuum (ultimately 0.1 mm Hg) at 30° C. The resulting residue was taken up in 75 mL of fresh THF and 10.2 g of HOBt (<5% $H_2O$ material) was added and dissolved in at room temperature.

An FTIR spectrum one hour after the addition indicated that the isomaleimide in the mixture had been largely, perhaps completely, consumed. Most of it appeared to have been converted to maleamic acid HOBt ester. The reaction mixture was stirred overnight. FTIR then indicated essentially complete conversion to the maleimide.

The solvent was stripped off at 30° C. and the residue extracted 2× with several hundred mL of pentane. The combined pentane fractions were chilled in a Dry Ice/isopropyl alcohol bath, which caused a white solid to crystallize out. (The solid is thought to be the acetate of HOBt, with some free HOBt). The pentane suspension was filtered cold, allowed to warm to room temperature, dried over anhydrous $MgSO_4$ and the solvent stripped to give 16.9 g (43.8%) of high purity product (as determined by FTIR).

EXAMPLE 2

Bismaleamic acid was generated from 10.0 g of Versamine 552 and 3.9 g of maleic anhydride, each in 40 mL of THF. 2-Ethoxy-1-ethoxycarbonyl-1,2-dihydroquinoline (EEDQ), 9.3 g, was added. Monitoring by FTIR indicated that two days sufficed to effect essentially complete conversion to isomaleimide. HOBt, 4.9 g, was dissolved in the reaction mixture. Monitoring by FTIR indicated that six hours sufficed to convert all the isoimide to imide. The solvent was stripped off and the residue extracted with pentane to yield 6.0 g of product bismaleimide, contaminated with quinoline from the EEDQ.

EXAMPLE 3

E. C. Martin and A. A. DeFusco, in U.S. Statutory Invention Registration No. H424 (Feb. 2, 1988) teach the preparation of bismaleimide from "dimer diamine" (source not given but material NOT having had the olefinic unsaturation removed) by means of HOBt and DCC. However, the maximum yield of bismaleimide reported is 50%. Thus, following the procedure of Martin and Fusco, the bismaleimide of Versamine 552 (Henkel Corp.) was prepared using dicyclohexylcarbodiimide (DCC) and 1-hydroxybenzotriazole (HOBt). A solution of 50.0 g (0.179 amine equiv) of Versamine 552 in 60 mL of anhydrous tetrahydrofuran (THF) was added slowly under argon atmosphere to a solution of 20.2 g (0.206 mole) of maleic anhydride in 300 mL of THF. The reaction mixture was stirred for an hour after completion of the addition and then 25.2 g (0.186 mole) of HOBt (<5% $H_2O$) was dissolved in. The stirred reaction mixture was chilled in an ice bath and melted DCC added neat in portions to a total of 49.2 g (0.238 mole). After completion of this addition, the reaction mixture was stirred in the ice bath for another hour. The ice bath was then removed and the stirred reaction mixture allowed to warm to room temperature overnight. The reaction mixture was filtered and the resulting solid was washed with THF. All THF phases were combined, 0.2 g methoxyphenol was added and the THF stripped on a rotary evaporator at 30° C. A thick, semisolid residue resulted. This residue was extracted with hexane and the hexane stripped to give 40.7 g (63.3%) of a product which still had some solid impurity. This material was extracted with pentane, which cleanly separated the solid impurity. The pentane extract was dried over $MgSO_4$ and the solvent stripped to give 32.1 g (49.9%) of lightly colored, low viscosity material with the expected FTIR spectrum.

EXAMPLE 3A

The monomaleimide of oleylamine was prepared using a method similar to the one described in Example 3. Oleylamine was obtained from Aldrich Chemical Company (Milwaukee, Wis.). The amine (40.0 grams, 150 meqs) was dissolved in 100 ml of anhydrous THF. This solution was slowly added (under an argon purge) to a mechanically stirred solution containing maleic anhydride (14.7 g, 150 meqs) dissolved in 100 ml of anhydrous THF. Stirring was continued for another hour after the addition was complete. The stirred reaction mixture was then cooled via an external ice bath and 30.8 g (149 meqs) dicyclohexylcarbodiimide (DCC), dissolved in 30 mls anhydrous THF, was added. The chilled mixture was stirred for an additional hour before 19.7 g (146 meqs) of 1-hydroxybenzotriazole (HOBt) was added. The mixture was allowed to warm up to room temperature while stirring was continued for another sixteen hours. The reaction mixture was filtered and the filtered residue was washed with additional THF. The combined THF solutions were stripped on a rotary evaporator at 40° C. until the pressure under full mechanical vacuum was ≦0.5 torr. The viscous residue was then dissolved in pentane. The pentane solution was extracted five times with 50 ml portions of aqueous methanol (70% MeOH). Magnesium sulfate was added to the washed pentane solution fraction and it was allowed to settle overnight in a refrigerator. The solution was warmed the next morning to room temperature, filtered, and the solvent stripped off in a rotary evaporator (using water aspirator, followed by full mechanical vacuum until the pressure remained ≦0.5 torr for one hour). The product recovered was a light brown, low viscosity liquid with an FTIR spectrum consistent with what one would predict for the expected structure.

EXAMPLE 3B

A diacrylate was prepared as follows from the dimer diol derived from oleic acid. This diol was obtained from Unichema North America (Chicago, Ill.) under the designation Pripol 2033. Approximately 53.8 grams of Pripol 2033 and 22.3 grams of triethylamine (reagent grade from Aldrich Chemical Co., Milwaukee, Wis.) were dissolved in 136.0 grams of dry acetone. This solution was chilled to 5° C. in an ice bath while the contents of the flask were blanketed under a slow argon purge. The solution was subjected to mechanical stirring while acroyl chloride (18.1 grams dissolved in 107.3 grams of dry acetone) was added dropwise over a two hour period. Stirring was continued for another hour and the bath was allowed to warm up to room temperature. Approximately 7.1 mg of methoxy hydroquinone (inhibitor) was added to the final reaction product and the acetone was removed on a rotary evaporator. The product was then dissolved in methylene chloride and this solution was then extracted three times with 7% aqueous sodium bicarbonate and another two times with 18 meg-ohm water. The solution was dried over magnesium sulfate and then filtered. Finally, the methylene chloride solvent was removed under full mechanical vacuum on the rotary evaporator. An FTIR analysis of this product showed a characteristic ester absorption around 1727 wave numbers. The final yield was 71% (based on the starting Pripol 2033).

EXAMPLE 4

This example illustrates improvement in yield obtained by using 3-hydroxy-1,2,3-benzotriazin-4-one (HOBtCO) instead of HOBt. The bismaleamic acid of Versamine 552 was prepared by the dropwise addition over an hour (dry argon atmosphere) of a solution of 144.0 g of Versamine 552 in 100 mL of dry dichloromethane ($CH_2Cl_2$) to a stirred solution of 50.4 g maleic anhydride in 300 mL of dry $CH_2Cl_2$ chilled in an ice bath. The ice bath was removed at the end of the addition and the reaction mixture stirred for another hour. The ice bath was then put back in place and 84.0 g (100%) of 3-hydroxy-1,2,3-benzotriazin-4-one was added. To the chilled reaction mixture was then added a solution of 106.1 g of DCC in 100 mL of $CH_2Cl_2$ over 30 minutes, with stirring. After completion of the addition, the ice bath was removed and the reaction mixture stirred overnight at room temperature. The reaction mixture was suction-filtered and the collected solid was washed twice with 100 mL portions of $CH_2Cl_2$, which were combined with the original $CH_2Cl_2$ filtrate. The $CH_2Cl_2$ was stripped on a rotary evaporator, at 35–40° C., ultimately under oil-pump vacuum (0.1 Torr). The resulting residue was extracted twice with 500 mL portions of pentane and once with a 1000 mL portion of pentane, all of which were combined and stripped on the rotary evaporator. The original residue was extracted with more pentane for a final total of four liters of pentane. After condensation to a volume of 500 mL, the solution was stored in the freezer overnight. It was allowed to warm to room temperature, suction-filtered through fine filter paper and the remaining pentane stripped to yield 145.0 g (80.0%) of the bismaleimide.

EXAMPLE 5

This example demonstrates that a very satisfactory yield may be obtained using much less than an equivalent of the coreactant compound, 3-hydroxy-1,2,3-benzotriazin-4-one (HOBtCO), and that it may be added after the DCC. The bismaleamic acid of Versamine 552 was generated as in Example 4 from 136.5 g of Versamine 552 and 46.3 g of maleic anhydride, except that the solvent was THF rather than $CH_2Cl_2$. To the chilled (ice bath) reaction mixture was added a THF solution of DCC containing 100.5 g of DCC. After an FTIR spectrum showed that the amic acid had been entirely converted to isoimide, 12 g (15%) of HOBtCO was added and the reaction mixture maintained at 45° C. for four hours, which sufficed, by FTIR, to convert the isoimide entirely to imide. Workup as in the preceding example resulted in a yield of 122 g (70%) of the bismaleimide.

EXAMPLE 6

This example illustrates the use of 1-hydroxy-7-aza-1,2-3-benzotriazole (HOAt) as the coreactant compound, again at a low level. Using the procedure described in the preceding example but with 20% HOAt, 51.5 g of Versamine 552 yielded 48.8 g (70.0%) of the BMI. Separation of the HOAt from the reaction product was facile and 4.4 g was recovered.

EXAMPLE 7

The following experiments demonstrate improvements in the yield, obtained by the procedure of Martin and Fusco by changes in procedure and protocol while still using HOBt. The procedure and protocol used is that detailed in Example 4 in which 3-hydroxy-1,2,3-benzotriazin-4-one is used except that the reaction solvent was THF in all cases here rather than the dichloromethane used in Example 4. A reaction using 100% HOBt gave a yield of 51.9%; four reactions using 80% HOBt gave yields of 56.8, 60.0, 65.1 and 70,2%, respectively. Also, a reaction employing dimer diamine in which the olefinic unsaturation has not been removed, as in U.S. Statutory Invention Registration No. H424 (Henkel Versamine 551 rather than 552), and 80% HOBt gave a yield of 52.2% of the corresponding BMI.

Examples 4–7 show that by variations in solvent and procedures, yields as high as 70% may be obtained using HOBt and as high as 80% using 3-hydroxy-1,2,3-benzotriazin-4-one (HOBtCO) in lieu of HOBt. Also the realization in the course of the present work that compounds such as HOBt and HOBtCO are potent agents for the isoimide to imide isomerization means that the reaction may be run with less than a full equivalent of such. The fact that such compounds are first consumed and then liberated during the cyclodehydration, and are thus in principle catalysts, does not of itself necessarily imply that they may be used at less than a full equivalent since the potentially competing reaction of direct cyclodehydration of the amic acid by DCC to the isoimide would still be of concern. However, as it turns out, HOBt, HOBtCO, and the like are effective at promoting the facile isomerization which leads to the desired product.

EXAMPLE 8

A masterbatch of the bisisomaleimide of Versamine 552 was prepared from 30.0 g of the amine, dissolved in 80 mL of anhydrous THF and added dropwise to a solution of 11.7 g of maleic anhydride in 100 mL of anhydrous THF to yield the bismaleamic acid, followed by the addition of 125 mL of neat acetic anhydride. One half of this reaction mixture was allowed to stand for three days at room temperature. The solvent and excess acetic anhydride were stripped to leave the isomaleimide. Portions of this isomaleimide were treated as follows. A 5.0 g sample was dissolved in anhydrous THF along with 2.6 g of 3-hydroxy-1,2,3-benzotriazin-4-one (HOBtCO). This solution was allowed to stand overnight, which sufficed to effect complete conversion to the maleimide, ultimately recovered in 56% yield. Another 5.0 g of the isomaleimide was treated with 2.3 g of HOBt in the same manner; a 46% yield of bismaleimide was recovered as well as a larger amount of oligomerized material than in the HBtCO reaction. A third portion of the isomaleimide, 4.9 g, was treated with 2.1 g of N-hydroxysuccinimide in acetonitrile solution. In this case, overnight reflux was used to effect conversion to the maleimide, recovered in only 36% yield.

EXAMPLE 9

A divinyl ether was prepared as follows from the dimer diol derived from oleic acid employing Pripol 2033 dimer diol obtained from Unichema North America (Chicago, Ill.), vinyl propyl ether obtained from BASF Corp. (Parsippany, N.J.), and palladium 1,10-phenanthroline diacetate [Pd(phen)(OAc)$_2$]. Thus, the Pripol was pre-dried over molecular sieves (3A) approximately 3 hours prior to use. Next, to a clean and dry 1 liter flask, with large oval Teflon stir bar, was added 149.1 grams (523.3 meqs) of Pripol 2033, 280 grams (3256 meqs) of vinyl propyl ether, and 1.0 grams Pd(phen)(AcO)$_2$ (2.5 meqs). The head space of the flask was purged with argon and the reaction flask fitted with an oil bubbler (to eliminate any pressure build up in the flask). The flask was placed on a magnetic stir plate and stirring initiated and continued for approximately 48 hours. The solution color changed from a light yellow to a deep dark brown. After 48 hours, an aliquot was removed and the bulk of the vinyl propyl ether was blown off using argon. An FTIR analysis was performed on the residue and it was determined that virtually all the alcohol had reacted (i.e., no OH absorbance between 3400 and 3500 cm$^{-1}$ remained).

To the original solution approximately 10–15 grams of activated charcoal was added. The solution was mixed for approximately 1 hour on the magnetic stir plate, then about 5 grams of Celite was added. The activated charcoal and Celite were removed via suction filtration through a fritted funnel packed with additional Celite (about an additional 15 grams). The solution that passed through the funnel retained a slight brown color.

The bulk of the excess vinyl propyl ether was then removed using a rotary evaporator at a bath temperature of 35–40° C. under a partial (water aspirator) vacuum. Once condensation stopped, the cold traps were emptied and replaced. A full mechanical vacuum was then applied and continued at the 35–40° C. bath temperature for approximately 1 hour. The vacuum decreased to under 1.0 torr within an hour. Product recovered at this point was a light brown, low viscosity liquid.

The last traces of propyl vinyl ether were removed using a falling film molecular still (operated at a strip temperature of 70° C. and a vacuum of less than one torr). The product residence time in the still head was about 15 to 20 minutes and the complete stripping procedure required about two hours. The product, following this strip, had no residual odor characteristic of the vinyl propyl ether. Thermogravimetric analysis showed no significant weight loss by 200° C. The product, therefore, was considered to be free of the vinyl ether starting material and any propyl alcohol co-product.

EXAMPLE 9A

A divinyl ether was prepared from an alpha-omega terminated, hydrogenated 1,2-polybutadiene. This diol had a molecular weight of approximately 3,000 grams per mole and was obtained from Ken Seika Corporation (Little Silver, N.J.) under the trade name GI-3000. The method used to synthesize the divinyl ether was analogous to the one described in Example 9. Approximately 51.5 grams (34.4 meqs) of GI-3000 was dissolved in 158.9 grams (1,840 meqs) of vinyl propyl ether. The mixture was stirred magnetically until a homogeneous solution was obtained. Palladium 1,10-phenanthroline diacetate (0.53 grams, 1.33 meqs) was then added and the entire mixture was allowed to stir for five days at room temperature under an argon atmosphere. An aliquot of the reaction product was removed and the volatiles (vinyl propyl ether and propanol) were blown off. An FTIR trace obtained on this residue demonstrated that the diol had been completely converted to the corresponding divinyl ether.

The bulk of the reaction product was then worked up according to the procedure described in the Example 9. The solution was decolorized using activated charcoal, treated with Celite, and the suspension was then passed through a filter packed with additional Celite. The bulk of the excess vinyl propyl ether and propanol were removed using a rotary evaporator (bath temperature ≦40° C.) at full mechanical pump vacuum. Evaporation was continued until the pressure fell to under one torr. The last traces of volatiles were stripped off using a falling film molecular still as described in Example 9. The final product was a viscous (although less so than the starting diol) straw colored liquid.

EXAMPLE 9B

Another oligomer diol was subjected to transvinylation. The alpha-omega diol of hydrogenated polyisoprene was employed for this example, and is available from Ken Seika Corporation under the designation "TH-21". This oligomer has an approximate molecular weight of 2,600 grams per mole. The same method as described in Example 9 was used to convert this diol to the corresponding divinyl ether. Thus, TH-21 (52.0 grams, 40 meqs) was dissolved in 83.7 grams of vinyl propyl ether (972 meqs) and 0.4 grams (1.0 meq) of palladium 1,10-phenanthroline diacetate catalyst was added. The mixture was stirred magnetically at room temperature under an argon atmosphere for six days. An evaporated aliquot of the reaction mixture was found to be essentially free of alcohol functionality according to FTIR analysis. The bulk of the reaction product was worked up as per the method described in Example 9. The final product was an amber, viscous liquid (again the viscosity of the divinyl compound was considerably lower in viscosity than the starting diol).

EXAMPLE 9C

Iso-eicosyl alcohol, obtained from M. Michel and Co., Inc. (New York, N.Y.) was transvinylated according to the method described in Example 9. The alcohol (100.3 grams. 336 meqs) was dissolved in 377.4 grams of the vinyl propyl ester (4,383 meqs) and 1.0 gram (2.5 meqs) of palladium 1,10-phenanthroline diacetate catalyst was added. The mixture was magnetically stirred under an argon atmosphere for four days. An FTIR trace of the evaporated reaction product showed that no detectable alcohol residue remained. The product was worked up as previously described. The final material was a pale yellow liquid with a "water-like" viscosity.

EXAMPLE 9D

Behenyl alcohol (1-docosanol), obtained from M. Michel and Co., Inc. (New York, N.Y.) was transvinylated substantially as described in Example 9, however, since the starting alcohol was a waxy solid with limited room temperature solubility in vinyl propyl ether, it was necessary to conduct the reaction at an elevated temperature. Thus, a mixture of the alcohol (100.8 grams, 309 meqs), vinyl propyl ether (406.0 grams, 4,714 meqs), and palladium 1,10-phenanthroline diacetate catalyst (1.0 gram, 2.5 meqs) was magnetically stirred at 50° C. under an argon atmosphere for 20 hours. Analysis of an evaporated aliquot after this period showed that no detectable alcohol remained. The behenyl vinyl ether was worked up as described above. The final product was an off-white waxy solid.

EXAMPLE 10

An organic adhesive vehicle was prepared using 2.78 grams (1.0 equivalents) of the BMI prepared according to Example 8, 0.94 grams (0.5 equivalents) of the divinyl ether prepared according to Example 9, and 0.58 grams (0.5 equivalents) of Vectomer 4010 (i.e., bis(4-vinyloxybutyl) isophthalate). An additional 1% by weight dicumyl peroxide (initiator), 0.5% gamma-methacryloxypropyltrimethoxysilane (coupling agent), and 0.5% beta-(3,4-epoxycyclohexyl)ethyltrimethoxysilane (coupling agent) were added to complete the organic adhesive mix.

Twenty-two percent by weight of the organic adhesive mixture was added to 78% by weight of silver metal filler. The mixture was stirred under high shear until homogeneous. The resulting paste was then degassed at 1 torr. The paste was dispensed onto silver plated copper lead frames using a starfish dispense nozzle. Bare silicon dice (300×300 mils on a side) were then placed on top and compressed into the adhesive until a 2.0 mil bondline had been attained (this process is virtually instantaneous when using automated "pick and place" equipment. The assembled parts were then cured on a heated surface (hot plate) controlled at 200° C. for two minutes. Additional void test parts (which were assembled in parallel using a 300×300 glass slide to replace the silicon die) showed the cured adhesive film to be free of voiding. Half of the assembled parts were subjected to tensile test immediately. The other half were placed in a pressure cooker at 121° C. for 168 hours (i.e., one week). The pressure cooker is considered to be a very aggressive test that has predictive value for the long term robustness of adhesives used in non-hermetic environments.

Adhesion strength testing was performed on these parts using a "Tinius Olsen 10,000" tensile test machine. Steel cube studs (0.25×0.25×0.8 inches) were attached at room temperature to the top of the die and the bottom of the lead frame using Loctite 415 cyanoacrylate glue. The cubes were attached using a V-block fixturing device to assure their co-linearity. Once the room temperature gluing operation was complete (~one hour later), the entire assembly was loaded into the tensile test machine. Pins were used to secure the steel blocks (through holes present in each of the test blocks) to the upper and lower arms of the stud pull machine. The tensile pull speed used was 3.00 inches per minute, and the adhesion measurement was recorded in terms of pounds of force. The tensile test results for the initial and post pressure cooker parts are presented in Table 1.

TABLE 1

| Initial Adhesion (lbs) | Retained Adhesion (lbs) |
| --- | --- |
| 191 | 141 |
| 169 | 147 |
| 179 | 112 |
| 180 | 153 |
| 166 | 126 |
| 155 | 138 |
| 174 | 161 |
| 175 | 121 |
| 111 | 133 |
| 149 | 149 |
| 164 | 154 |
| 144 | 119 |

As the results in Table 1 demonstrate, the product was found to have good initial and retained adhesion. The average adhesion for the parts prior to pressure cooker treatment was 163 pounds and after pressure cooker it was 138 pounds. Thus, even after one full week at two atmospheres pressure of steam (14.7 psig, 121° C.) about 85% of the initial adhesion was retained. It is noteworthy that a competitive material which was run at the same time had an initial adhesion of 338 pounds, but dropped down to zero after the pressure cooker treatment.

EXAMPLE 10A

A composition was formulated using a monovinyl ether diluent and a divinyl ether "rubber" comonomer. The addition of these materials was used to enhance certain properties of the adhesive composition. Specifically, the monovinyl ether was used to reduce the viscosity and increase the thixotropic index (defined as the quotient of the 1 rpm over the 20 rpm viscosity). The "rubber" comonomer was used to "flexibilize" the cured adhesive. Flexibility is especially important when thin bondlines are used since stress increases as bondline decreases. A convenient measure of stress for a cured part is the radius of curvature (ROC). This measurement is traditionally done with a surface profilometer and is an index of the "bowing" of the silicon die. The higher the ROC (i.e., the larger the sphere described by measured arc) the lower the stress. It is generally desirable to have an ROC≧one meter. The composition described in Example 10 results in a radius of curvature of greater than 1.5 meters when used at a 2.0 mil bondline, but gives a ROC of less than one meter when the bondline is reduced to 1.0 mils.

The monovinyl ether diluent used, vinyl octadecyl ether, was purchased from BASF Corp. (Parsippany, N.J.). The divinyl ether "rubber" was the product described in Example 9B. An organic adhesive vehicle was prepared using 1.29 grams (3.7 meqs) of the BMI prepared according to Example 8, 0.1125 grams (0.38 meqs) vinyl octadecyl ether, and 0.1127 grams (0.08 meqs) of the divinyl ether prepared according to Example 9B. An additional 1.0% by weight dicumyl peroxide (initiator) and 2.7% gamma-methacryloxy-propyltrimethoxysilane coupling agent were added to complete the organic adhesive mix.

Twenty-seven percent by weight of the above organic adhesive mixture was added to 73% by weight of silver filler. The mixture was homogenized under high shear and then degassed using a full mechanical pump vacuum. The adhesive was dispensed into silver plated copper lead frames using a starfish dispense nozzle. Bare silicon dice (300×300 mil on a side) were placed on top and compressed into the adhesive to achieve a 1.0 mil bondline. A similar set of parts was generated using the adhesive composition described in Example 10. The parts were cured for one minute at 200° C. The radius of curvature for parts using the adhesive described here was 1.29 meters. The ROC for the control parts was 0.76 meters. The 10 rpm viscosity (Brookfield viscometer) for the adhesive described here was 5,734 centipoise at 25.0° C. and the thixotropic index was 6.60. The control adhesive had a 12,040 10 rpm viscosity at 25.0° C. and a thixotropic index of 4.97. The post cure adhesion results for the adhesive described here and the control were as follows:

TABLE 2

| Adhesion for Test Paste (lbs) | Adhesion for Control (lbs) |
|---|---|
| 157 | 72 |
| 149 | 139 |
| 154 | 175 |
| 134 | 149 |
| 158 | 97 |
| 159 | 136 |

The results presented here demonstrate that several of the adhesive composition properties can be improved with little or no sacrifice of initial adhesion by the incorporation of modest amounts of a reactive diluent and a flexibilizing comonomer.

EXAMPLE 10B

The previous examples demonstrated how adhesive compositions could be formulated in which no more than one equivalent of vinyl ether comonomer is used in conjunction with an excess of a bismaleimide. It is not necessary to have any vinyl ether present in the composition, however. That is to say, that compositions may be formulated where maleimide is the only polymerizable function.

Thus, an organic adhesive vehicle was prepared using 96.25% by weight of the BMI prepared according to Example 8, 1% by weight USP90MD [1,1bis(t-amyl peroxy) cyclohexane—an initiator available from Witco Corporation, Marshall, Tex.], 0.76% gamma-methacryloxypropyl-trimethoxysilane (coupling agent), and 1.72% beta-(3,4-epoxycyclohexyl)ethyltrimethoxysilane (coupling agent).

Twenty-five percent by weight of the above organic adhesive mixture was added to 75% by weight of silver metal filler. The mixture was sheared and degassed as before. Dispense and die placement were performed as described earlier (300×300 mil silicon die on Ag coated Cu lead frames). The bondline used was 1.0 mils and the cure time was one minute at 200° C. Initial and post pressure cooker (16 hour) adhesion values are presented in the following table.

TABLE 3

| Initial Adhesion (lbs) | Post Pressure Cooker Adhesion (lbs) |
|---|---|
| 165 | 83 |
| 137 | 188 |
| 115 | 143 |
| 171 | 122 |
| 148 | 208 |
| 154 | 200 |

This composition exhibited a narrow exotherm with a maxima at 128.8° C. via differential scanning calorimetry (DSC) and a weight loss of less than 0.75% by 350° C. according to TGA (10° C./min. using an air purge). This composition therefore demonstrates the viability of an "all maleimidel" snap cure adhesive system.

EXAMPLE 10C

The previous examples have demonstrated the utility of maleimide/vinyl ether co-cure and maleimide homocure for use as adhesives. Other polymerizable functional groups including acrylate and methacrylate may also be used alone or in combination with maleimide and/or vinyl ether monomers.

Thus, an organic adhesive vehicle was prepared using 4.00 grams of the diacrylate prepared according to Example 3B, 1.00 gram decanediol dimethacrylate (purchased from Polysciences, Inc., Warrington, Pa.), and 1.00 gram Ricon R-130 Epoxy (obtained from Advanced Resins, Inc., Grand Junction, Colo.). Two percent by weight of dicumyl peroxide initiator was dissolved in this mix.

Twenty percent by weight of the organic adhesive mixture was added to 80% by weight silver metal filler. The mixture was homogenized using high shear and then degassed. Parts were assembled as before using 300×300 silicon on Ag plated Cu lead frames. The cure condition was 200° C. for one minute, and the bondline thickness used was 1.0 mil. The initial adhesion values an the corresponding failure mode information is presented in the following table:

TABLE 4

| Initial Adhesion (lbs) | Failure Mode (lbs) |
|---|---|
| 66 | material |
| 55 | material |
| 67 | material |
| 62 | material |
| 63 | material |
| 59 | material |

The measured adhesion for this mixture was lower than observed for most of the BMI containing compositions. The failure mode, however, was of the most preferred (all material) type (i.e., entirely cohesive rather than adhesive failure). The radius of curvature for the cured adhesive at the bondline thickness used here was 2.51 meters.

EXAMPLE 11

A test paste was made that contained one equivalent each of the bismaleimide of Versalink 650 (polytetramethyleneoxide-di-p-aminobenzoate, marketed by Air Products, Allentown, Pa.) and the divinyl ether of tetraethylene glycol. The organic phase had 1% by weight of dicumyl peroxide. Seventy-five percent by weight silver filler was used in the paste. Ten parts were assembled and cured as per the preceding example using this paste that contained no coupling agent. One percent by weight of the same mixed coupling agents noted above were then added to the paste. Another ten parts were assembled and cured using this new paste mix. Both groups of parts were then divided into two sets. Half of the parts from each group was tested for tensile strength immediately and the other half following four hours of immersion in the pressure cooker. Tensile strength measurements were performed according to the procedure described in Example 10. The results of this testing are summarized in Table 5.

TABLE 5

| Tensile Strength of Adhesive Bond | | | |
|---|---|---|---|
| No Coupling Agent | | With Coupling Agent | |
| Initial Value | Post Moisture | Initial Value | Post Moisture |
| 110.7 | 0 | 112.3 | 88.8 |
| 111.2 | 0 | 102.6 | 84.3 |
| 107.7 | 0 | 108.5 | 83.8 |

TABLE 5-continued

Tensile Strength of Adhesive Bond

| No Coupling Agent | | With Coupling Agent | |
| --- | --- | --- | --- |
| Initial Value | Post Moisture | Initial Value | Post Moisture |
| 110.5 | 0 | 109.2 | 87.9 |
| 106.5 | 0 | 115.6 | 93.3 |

The data in Table 5 shows that the presence of the coupling agents has a dramatic impact on the survival of the adhesive bond in extreme moisture environments.

EXAMPLE 12

A test was conducted to test the adhesion performance of invention compositions following a one minute cure at 200° C. The bondline used for these parts was also dropped from 2.0 down to 1.0 mils during the attach step. Stress, which is induced by the large thermal mismatch between the silicon and lead frame, increases when the bondline is decreased. The organic adhesive portion of paste consisted of one equivalent each of the BMI prepared according to Example 8, and Vectomer 4010 (i.e., bis(4-vinyloxybutyl) isophthalate). It also contained 4.5% of gamma-methacryloxypropyl-trimethoxysilane coupling agent, as well as 0.95% dicumyl peroxide initiator. A paste was made consisting of 22% by weight of this adhesive composition and 78% by weight of silver flake. The paste was degassed and then used to attach 300×300 mil silicon die to silver plated copper lead frames using the reduced bondline and cure time. Six parts were assembled and cured. Two void test parts (same conditions but using 300×300 mil glass slides to replace the silicon die) were also made. There was no evidence of porosity in the void test parts. Tensile strength measurements were performed according to the procedure described in Example 10. The tensile test values for the other parts were: 116, 114, 119, 122, 128 and 134 pounds force.

While the invention has been described in detail with reference to certain preferred embodiments thereof, it will be understood that modifications and variations are within the spirit and scope of that which is described and claimed.

That which is claimed is:

1. A maleimide composition comprising
   (a) a liquid maleimide; and
   (b) a peroxide cure initiator,
   wherein said maleimide composition, when dispensed between a 300×300 mil silica die and a Ag coated lead frame as a 1 mil bondline and cured for 1 minute at a temperature of about 200° C., demonstrates an initial adhesion value of at least 115 lbs.

2. The composition of claim 1, substantially free of inert diluent.

3. A composition comprising
   (a) a liquid maleimide comprising:

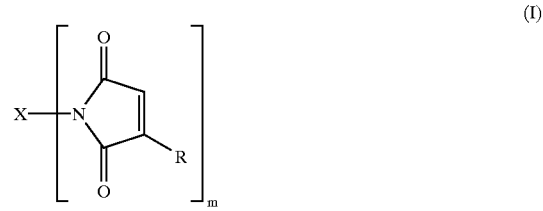

wherein:
   each R is independently hydrogen or lower alkyl,
   —X— is a branched chain alkyl or alkylene species having at least 12 carbon atoms, and
   m is 1, 2 or 3;
   (b) a peroxide cure initiator.

4. An assembly comprising a first article permanently adhered to a second article by a cured aliquot of the composition of claim 1.

5. An assembly comprising a first article permanently adhered to a second article by a cured aliquot of the composition of claim 3.

6. The composition of claim 1, further comprising a filler.

7. The composition of claim 3, further comprising a filler.

8. The composition of claim 3, substantially free of inert diluent.

9. The composition of claim 4, wherein the first article is a silicon die.

10. The composition of claim 5, wherein the first article is a silicon die.

11. The maleimide composition according to either claim 1 or 2, which exhibits a post pressure cooker adhesion of at least 83 lbs.

* * * * *

UNITED STATES PATENT AND TRADEMARK OFFICE
CERTIFICATE OF CORRECTION

PATENT NO.    : 6,852,814 B2
DATED         : February 8, 2005
INVENTOR(S)   : Stephen M. Dershem et al.

It is certified that error appears in the above-identified patent and that said Letters Patent is hereby corrected as shown below:

Title page,
Item [73], Assignee, "Henkel Corporation, CT (US)" should read -- Henkel Corporation, Rocky Hill, CT (US) --.

Column 5,
Line 40, "with in" should read -- within --.

Column 8,
Line 49, "with in" should read -- within --.

Column 9,
Line 4, "with in" should read -- within --.

Column 19,
Line 42, "Ag coated" should read -- Ag-coated --.

Column 20,
Line 15, "Ag" should read -- Ag- --.

Column 21,
Line 18, "one minute" should read -- one-minute --; and
Line 46, "comprising" should read -- , comprising: --.

UNITED STATES PATENT AND TRADEMARK OFFICE
CERTIFICATE OF CORRECTION

PATENT NO.   : 6,852,814 B2
DATED         : February 8, 2005
INVENTOR(S)  : Stephen M. Dershem et al.

It is certified that error appears in the above-identified patent and that said Letters Patent is hereby corrected as shown below:

Column 22,
Line 3, "a Ag coated" should read -- an Ag-coated --;
Line 9, "comprising" should read -- , comprising: --; and
Line 39, "composition" should read -- assembly --.

Signed and Sealed this

Twenty-eighth Day of June, 2005

JON W. DUDAS
*Director of the United States Patent and Trademark Office*